United States Patent [19]

Mehta et al.

[11] Patent Number: 5,308,750
[45] Date of Patent: May 3, 1994

[54] MONOCLONAL ANTIBODIES TO PUTATIVE HCV E2/NS1 PROTEINS AND METHODS FOR USING SAME

[75] Inventors: Smriti U. Mehta, Libertyville; Jill E. Johnson, Waukegan; Stephen H. Dailey, Vernon Hills; Suresh M. Desai, Libertyville; Sushil G. Devare, Northbrook, all of Ill.

[73] Assignee: Abbott Laboratories, Abbott Park, Ill.

[21] Appl. No.: 748,292

[22] Filed: Aug. 21, 1991

Related U.S. Application Data

[63] Continuation-in-part of Ser. No. 610,180, Nov. 7, 1990, abandoned, and Ser. No. 456,162, Dec. 22, 1989, abandoned.

[51] Int. Cl.$^5$ .......................... C12N 5/00; C12Q 1/70
[52] U.S. Cl. .................................... 435/5; 435/240.27; 436/548; 436/820; 530/388.3
[58] Field of Search ............... 435/5, 70.21, 172.2; 435/240.27; 530/388.3; 436/548, 518, 820

[56] References Cited

U.S. PATENT DOCUMENTS 5,106,726  4/1992  Wang .................................. 435/5

FOREIGN PATENT DOCUMENTS 0318216  5/1989  European Pat. Off. .

Primary Examiner—Esther L. Kepplinger
Assistant Examiner—Donna C. Wortman
Attorney, Agent, or Firm—Priscilla E. Porembski

[57] ABSTRACT

Monoclonal antibodies which specifically bind to Hepatitis C Virus (HCV) E2/NS1 antigen. Also provided are hybridoma cell lines which secrete these monoclonal antibodies, methods for using these monoclonal antibodies, and assay kits for assays 7hich contain these monoclonal antibodies.

13 Claims, 4 Drawing Sheets

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
    ( A ) LENGTH: 121 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

```
Gly Pro Trp Ile Thr Pro Arg Cys Leu Val Asp Tyr Pro Tyr Arg Leu
1               5                   10                  15

Trp His Tyr Pro Cys Thr Ile Asn Tyr Thr Ile Phe Lys Ile Arg Met
                20                  25                  30

Tyr Val Gly Gly Val Glu His Arg Leu Glu Ala Ala Cys Asn Trp Thr
            35                  40                  45

Arg Gly Glu Arg Cys Asp Leu Glu Asp Arg Asp Arg Ser Glu Leu Ser
    50                  55                  60

Pro Leu Leu Leu Thr Thr Thr Gln Trp Gln Val Leu Pro Cys Ser Phe
65                  70                  75                  80

Thr Thr Leu Pro Ala Leu Ser Thr Gly Leu Ile His Leu His Gln Asn
                85                  90                  95

Ile Val Asp Val Gln Tyr Leu Tyr Gly Val Gly Ser Ser Ile Ala Ser
                100                 105                 110

Trp Ala Ile Lys Trp Glu Tyr Val Val
                115                 120
```

( 2 ) INFORMATION FOR SEQ ID NO:2:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

```
Cys Leu Val Asp Tyr Pro Tyr Arg Leu Trp His Tyr Pro Cys Thr Ile
1               5                   10                  15

Asn Tyr Thr Ile Phe
                20
```

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ala Cys Asn Trp Thr Arg Gly Glu Arg Cys Asp Leu Glu Asp Arg Asp
 1               5                  10                  15

Arg Ser Glu Leu Ser
             20
```

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Leu Leu Thr Thr Thr Gln Trp Gln Val Leu Pro Cys Ser Phe Thr Thr
 1               5                  10                  15

Leu Pro
```

( 2 ) INFORMATION FOR SEQ ID NO:5:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Gln Trp Gln Val Leu Pro Cys Ser Phe Thr Thr Leu Pro Ala Leu Ser
 1               5                  10                  15

Thr Gly Leu Ile His
             20
```

( 2 ) INFORMATION FOR SEQ ID NO:6:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Ala Cys Asn Trp Thr Arg Gly Glu Arg Cys Asp Leu Glu Asp Arg Asp
 1               5                  10                  15

Arg Ser Glu Leu Ser Pro Leu Leu Leu Thr Thr Thr Gln Trp Gln Val
             20                  25                  30

Leu Pro Cys Ser Phe Thr Thr Leu Pro
             35                  40
```

( 2 ) INFORMATION FOR SEQ ID NO:7:

(i) SEQUENCE CHARACTERISTICS:
  (A) LENGTH: 621 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:7:

```
Met  Ser  Phe  Val  Val  Ile  Ile  Pro  Ala  Arg  Tyr  Ala  Ser  Thr  Arg  Leu
 1              5                        10                       15

Pro  Gly  Lys  Pro  Leu  Val  Asp  Ile  Asn  Gly  Lys  Pro  Met  Ile  Val  His
              20                        25                       30

Val  Leu  Glu  Arg  Ala  Arg  Glu  Ser  Gly  Ala  Glu  Arg  Ile  Ile  Val  Ala
         35                        40                       45

Thr  Asp  His  Glu  Asp  Val  Ala  Arg  Ala  Val  Glu  Ala  Ala  Gly  Gly  Glu
    50                        55                       60

Val  Cys  Met  Thr  Arg  Ala  Asp  His  Gln  Ser  Gly  Thr  Glu  Arg  Leu  Ala
65                       70                        75                       80

Glu  Val  Val  Glu  Lys  Cys  Ala  Phe  Ser  Asp  Asp  Thr  Val  Ile  Val  Asn
              85                        90                       95

Val  Gln  Gly  Asp  Glu  Pro  Met  Ile  Pro  Ala  Thr  Ile  Ile  Arg  Gln  Val
              100                       105                     110

Ala  Asp  Asn  Leu  Ala  Gln  Arg  Gln  Val  Gly  Met  Thr  Thr  Leu  Ala  Val
              115                       120                     125

Pro  Ile  His  Asn  Ala  Glu  Glu  Ala  Phe  Asn  Pro  Asn  Ala  Val  Lys  Val
         130                       135                     140

Val  Leu  Asp  Ala  Glu  Gly  Tyr  Ala  Leu  Tyr  Phe  Ser  Arg  Ala  Thr  Ile
145                           150                       155                     160

Pro  Trp  Asp  Arg  Asp  Arg  Phe  Ala  Glu  Gly  Leu  Glu  Thr  Val  Gly  Asp
              165                       170                     175

Asn  Phe  Leu  Arg  His  Leu  Gly  Ile  Tyr  Gly  Tyr  Arg  Ala  Gly  Phe  Ile
              180                       185                     190

Arg  Arg  Tyr  Val  Asn  Trp  Gln  Pro  Ser  Pro  Leu  Glu  His  Ile  Glu  Met
         195                       200                     205

Leu  Glu  Gln  Leu  Arg  Val  Leu  Trp  Tyr  Gly  Glu  Lys  Ile  His  Val  Ala
    210                       215                     220

Val  Ala  Gln  Glu  Val  Pro  Gly  Thr  Gly  Val  Asp  Thr  Pro  Glu  Asp  Leu
225                           230                       235                     240

Asp  Pro  Ser  Thr  Asn  Ser  Thr  Met  Val  Gly  Asn  Trp  Ala  Lys  Val  Leu
              245                       250                     255

Val  Val  Leu  Leu  Leu  Phe  Ala  Gly  Val  Asp  Ala  Glu  Thr  His  Val  Thr
              260                       265                     270

Gly  Gly  Ser  Ala  Gly  His  Thr  Val  Ser  Gly  Phe  Val  Ser  Leu  Leu  Ala
         275                       280                     285

Pro  Gly  Ala  Lys  Gln  Asn  Val  Gln  Leu  Ile  Asn  Thr  Asn  Gly  Ser  Trp
    290                       295                     300

His  Leu  Asn  Ser  Thr  Ala  Leu  Asn  Cys  Asn  Asp  Ser  Leu  Asn  Thr  Gly
305                           310                       315                     320

Trp  Leu  Ala  Gly  Leu  Phe  Tyr  His  His  Lys  Phe  Asn  Ser  Ser  Gly  Cys
              325                       330                     335

Pro  Glu  Arg  Leu  Ala  Ser  Cys  Arg  Pro  Leu  Thr  Asp  Phe  Asp  Gln  Gly
              340                       345                     350

Trp  Gly  Gln  Ile  Ser  Tyr  Ala  Asn  Gly  Ser  Gly  Pro  Asp  Gln  Arg  Pro
         355                       360                     365

Tyr  Cys  Trp  His  Tyr  Pro  Pro  Lys  Pro  Cys  Gly  Ile  Val  Pro  Ala  Lys
    370                       375                     380
```

```
Ser  Val  Cys  Gly  Pro  Val  Tyr  Cys  Phe  Thr  Pro  Ser  Pro  Val  Val  Val
385            390                      395                           400

Gly  Thr  Thr  Asp  Arg  Ser  Gly  Ala  Pro  Thr  Tyr  Ser  Trp  Gly  Glu  Asn
               405                      410                      415

Asp  Thr  Asp  Val  Phe  Val  Leu  Asn  Asn  Thr  Arg  Pro  Pro  Leu  Gly  Asn
               420                      425                      430

Trp  Phe  Gly  Cys  Thr  Trp  Met  Asn  Ser  Thr  Gly  Phe  Thr  Lys  Val  Cys
          435                      440                      445

Gly  Ala  Pro  Pro  Cys  Val  Ile  Gly  Pro  Pro  Cys  Val  Ile  Gly  Gly  Ala
          450                      455                 460

Gly  Asn  Asn  Thr  Leu  His  Cys  Pro  Thr  Asp  Cys  Phe  Arg  Lys  His  Pro
465                      470                 475                           480

Asp  Ala  Thr  Tyr  Ser  Arg  Cys  Gly  Ser  Gly  Pro  Trp  Ile  Thr  Pro  Arg
                    485                      490                      495

Cys  Leu  Val  Asp  Tyr  Pro  Tyr  Arg  Leu  Trp  His  Tyr  Pro  Cys  Thr  Ile
               500                      505                 510

Asn  Tyr  Thr  Ile  Phe  Lys  Ile  Arg  Met  Tyr  Val  Gly  Gly  Val  Glu  His
          515                      520                      525

Arg  Leu  Glu  Ala  Ala  Cys  Asn  Trp  Thr  Arg  Gly  Glu  Arg  Cys  Asp  Leu
     530                      535                      540

Glu  Asp  Arg  Asp  Arg  Ser  Glu  Leu  Ser  Pro  Leu  Leu  Leu  Thr  Thr  Thr
545                      550                      555                      560

Gln  Trp  Gln  Val  Leu  Pro  Cys  Ser  Phe  Thr  Thr  Leu  Pro  Ala  Leu  Ser
               565                      570                      575

Thr  Gly  Leu  Ile  His  Leu  His  Gln  Asn  Ile  Val  Asp  Val  Gln  Tyr  Leu
               580                      585                      590

Tyr  Gly  Val  Gly  Ser  Ser  Ile  Ala  Ser  Trp  Ala  Ile  Lys  Trp  Glu  Tyr
               595                      600                      605

Val  Val  Leu  Leu  Phe  Leu  Leu  Leu  Ala  Asp  Ala  Arg  Val
610                      615                      620
```

( 2 ) INFORMATION FOR SEQ ID NO:8:

( i ) SEQUENCE CHARACTERISTICS:
        ( A ) LENGTH: 414 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Met  Ser  Phe  Val  Val  Ile  Ile  Pro  Ala  Arg  Tyr  Ala  Ser  Thr  Arg  Leu
1              5                        10                      15

Pro  Gly  Lys  Pro  Leu  Val  Asp  Ile  Asn  Gly  Lys  Pro  Met  Ile  Val  His
          20                      25                 30

Val  Leu  Glu  Arg  Ala  Arg  Glu  Ser  Gly  Ala  Glu  Arg  Ile  Ile  Val  Ala
          35                      40                      45

Thr  Asp  His  Glu  Asp  Val  Ala  Arg  Ala  Val  Glu  Ala  Ala  Gly  Gly  Glu
     50                      55                      60

Val  Cys  Met  Thr  Arg  Ala  Asp  His  Gln  Ser  Gly  Thr  Glu  Arg  Leu  Ala
65                       70                 75                           80

Glu  Val  Val  Glu  Lys  Cys  Ala  Phe  Ser  Asp  Asp  Thr  Val  Ile  Val  Asn
               85                      90                      95

Val  Gln  Gly  Asp  Glu  Pro  Met  Ile  Pro  Ala  Thr  Ile  Ile  Arg  Gln  Val
               100                     105                     110

Ala  Asp  Asn  Leu  Ala  Gln  Arg  Gln  Val  Gly  Met  Thr  Thr  Leu  Ala  Val
               115                     120                     125
```

| Pro | Ile | His | Asn | Ala | Glu | Glu | Ala | Phe | Asn | Pro | Asn | Ala | Val | Lys | Val |
|---|---|---|---|---|---|---|---|---|---|---|---|---|---|---|---|
| | 130 | | | | 135 | | | | | 140 | | | | | |

| Val | Leu | Asp | Ala | Glu | Gly | Tyr | Ala | Leu | Tyr | Phe | Ser | Arg | Ala | Thr | Ile |
|---|---|---|---|---|---|---|---|---|---|---|---|---|---|---|---|
| 145 | | | | | 150 | | | | | 155 | | | | | 160 |

| Pro | Trp | Asp | Arg | Asp | Arg | Phe | Ala | Glu | Gly | Leu | Glu | Thr | Val | Gly | Asp |
|---|---|---|---|---|---|---|---|---|---|---|---|---|---|---|---|
| | | | | 165 | | | | | 170 | | | | | 175 | |

| Asn | Phe | Leu | Arg | His | Leu | Gly | Ile | Tyr | Gly | Tyr | Arg | Ala | Gly | Phe | Ile |
|---|---|---|---|---|---|---|---|---|---|---|---|---|---|---|---|
| | | | 180 | | | | | 185 | | | | | 190 | | |

| Arg | Arg | Tyr | Val | Asn | Trp | Gln | Pro | Ser | Pro | Leu | Glu | His | Ile | Glu | Met |
|---|---|---|---|---|---|---|---|---|---|---|---|---|---|---|---|
| | | 195 | | | | | 200 | | | | | 205 | | | |

| Leu | Glu | Gln | Leu | Arg | Val | Leu | Trp | Tyr | Gly | Glu | Lys | Ile | His | Val | Ala |
|---|---|---|---|---|---|---|---|---|---|---|---|---|---|---|---|
| | 210 | | | | | 215 | | | | | 220 | | | | |

| Val | Ala | Gln | Glu | Val | Pro | Gly | Thr | Gly | Val | Asp | Thr | Pro | Glu | Asp | Leu |
|---|---|---|---|---|---|---|---|---|---|---|---|---|---|---|---|
| 225 | | | | | 230 | | | | | 235 | | | | | 240 |

| Asp | Pro | Ser | Thr | Asn | Ser | Met | Gly | Ala | Pro | Pro | Cys | Val | Ile | Gly | Gly |
|---|---|---|---|---|---|---|---|---|---|---|---|---|---|---|---|
| | | | | 245 | | | | | 250 | | | | | 255 | |

| Ala | Gly | Asn | Asn | Thr | Leu | His | Cys | Pro | Thr | Asp | Cys | Phe | Arg | Lys | His |
|---|---|---|---|---|---|---|---|---|---|---|---|---|---|---|---|
| | | | 260 | | | | | 265 | | | | | 270 | | |

| Pro | Asp | Ala | Thr | Tyr | Ser | Arg | Cys | Gly | Ser | Gly | Pro | Trp | Ile | Thr | Pro |
|---|---|---|---|---|---|---|---|---|---|---|---|---|---|---|---|
| | | 275 | | | | | 280 | | | | | 285 | | | |

| Arg | Cys | Leu | Val | Asp | Tyr | Pro | Tyr | Arg | Leu | Trp | His | Tyr | Pro | Cys | Thr |
|---|---|---|---|---|---|---|---|---|---|---|---|---|---|---|---|
| | 290 | | | | | 295 | | | | | 300 | | | | |

| Ile | Asn | Tyr | Thr | Ile | Phe | Lys | Ile | Arg | Met | Tyr | Val | Gly | Gly | Val | Glu |
|---|---|---|---|---|---|---|---|---|---|---|---|---|---|---|---|
| 305 | | | | | 310 | | | | | 315 | | | | | 320 |

| His | Arg | Leu | Glu | Ala | Ala | Cys | Asn | Trp | Thr | Arg | Gly | Glu | Arg | Cys | Asp |
|---|---|---|---|---|---|---|---|---|---|---|---|---|---|---|---|
| | | | | 325 | | | | | 330 | | | | | 335 | |

| Leu | Glu | Asp | Arg | Asp | Arg | Ser | Glu | Leu | Ser | Pro | Leu | Leu | Leu | Thr | Thr |
|---|---|---|---|---|---|---|---|---|---|---|---|---|---|---|---|
| | | | 340 | | | | | 345 | | | | | 350 | | |

| Thr | Gln | Trp | Gln | Val | Leu | Pro | Cys | Ser | Phe | Thr | Thr | Leu | Pro | Ala | Leu |
|---|---|---|---|---|---|---|---|---|---|---|---|---|---|---|---|
| | | 355 | | | | | 360 | | | | | 365 | | | |

| Ser | Thr | Gly | Leu | Ile | His | Leu | His | Gln | Asn | Ile | Val | Asp | Val | Gln | Tyr |
|---|---|---|---|---|---|---|---|---|---|---|---|---|---|---|---|
| | 370 | | | | | 375 | | | | | 380 | | | | |

| Leu | Tyr | Gly | Val | Gly | Ser | Ser | Ile | Ala | Ser | Trp | Ala | Ile | Lys | Trp | Glu |
|---|---|---|---|---|---|---|---|---|---|---|---|---|---|---|---|
| 385 | | | | | 390 | | | | | 395 | | | | | 400 |

| Tyr | Val | Val | Leu | Leu | Phe | Leu | Leu | Leu | Ala | Asp | Ala | Arg | Val |
|---|---|---|---|---|---|---|---|---|---|---|---|---|---|
| | | | | 405 | | | | | 410 | | | | |

( 2 ) INFORMATION FOR SEQ ID NO:9:

( i ) SEQUENCE CHARACTERISTICS:
        ( A ) LENGTH: 463 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

| Met | Ser | Phe | Val | Val | Ile | Ile | Pro | Ala | Arg | Tyr | Ala | Ser | Thr | Arg | Leu |
|---|---|---|---|---|---|---|---|---|---|---|---|---|---|---|---|
| 1 | | | | 5 | | | | | 10 | | | | | 15 | |

| Pro | Gly | Lys | Pro | Leu | Val | Asp | Ile | Asn | Gly | Lys | Pro | Met | Ile | Val | His |
|---|---|---|---|---|---|---|---|---|---|---|---|---|---|---|---|
| | | | 20 | | | | | 25 | | | | | 30 | | |

| Val | Leu | Glu | Arg | Ala | Arg | Glu | Ser | Gly | Ala | Glu | Arg | Ile | Ile | Val | Ala |
|---|---|---|---|---|---|---|---|---|---|---|---|---|---|---|---|
| | | 35 | | | | | 40 | | | | | 45 | | | |

| Thr | Asp | His | Glu | Asp | Val | Ala | Arg | Ala | Val | Glu | Ala | Ala | Gly | Gly | Glu |
|---|---|---|---|---|---|---|---|---|---|---|---|---|---|---|---|
| | 50 | | | | | 55 | | | | | 60 | | | | |

| Val | Cys | Met | Thr | Arg | Ala | Asp | His | Gln | Ser | Gly | Thr | Glu | Arg | Leu | Ala |
|---|---|---|---|---|---|---|---|---|---|---|---|---|---|---|---|
| 65 | | | | | 70 | | | | | 75 | | | | | 80 |

| | | | | | | | | | | | | | | |
|---|---|---|---|---|---|---|---|---|---|---|---|---|---|---|
| Glu | Val | Val | Glu | Lys<br>85 | Cys | Ala | Phe | Ser | Asp<br>90 | Thr | Val | Ile | Val<br>95 | Asn |
| Val | Gln | Gly | Asp<br>100 | Glu | Pro | Met | Ile | Pro<br>105 | Ala | Thr | Ile | Ile | Arg<br>110 | Gln | Val |
| Ala | Asp | Asn<br>115 | Leu | Ala | Gln | Arg | Gln<br>120 | Val | Gly | Met | Thr | Thr<br>125 | Leu | Ala | Val |
| Pro | Ile<br>130 | His | Asn | Ala | Glu | Glu<br>135 | Ala | Phe | Asn | Pro | Asn<br>140 | Ala | Val | Lys | Val |
| Val<br>145 | Leu | Asp | Ala | Glu | Gly<br>150 | Tyr | Ala | Leu | Tyr | Phe<br>155 | Ser | Arg | Ala | Thr | Ile<br>160 |
| Pro | Trp | Asp | Arg | Asp<br>165 | Arg | Phe | Ala | Glu | Gly<br>170 | Leu | Glu | Thr | Val | Gly<br>175 | Asp |
| Asn | Phe | Leu | Arg<br>180 | His | Leu | Gly | Ile | Tyr<br>185 | Gly | Tyr | Arg | Ala | Gly<br>190 | Phe | Ile |
| Arg | Arg | Tyr<br>195 | Val | Asn | Trp | Gln | Pro<br>200 | Ser | Pro | Leu | Glu | His<br>205 | Ile | Glu | Met |
| Leu | Glu<br>210 | Gln | Leu | Arg | Val | Leu<br>215 | Trp | Tyr | Gly | Glu | Lys<br>220 | Ile | His | Val | Ala |
| Val<br>225 | Ala | Gln | Glu | Val | Pro<br>230 | Gly | Thr | Gly | Val | Asp<br>235 | Thr | Pro | Glu | Asp | Leu<br>240 |
| Asp | Pro | Ser | Thr | Asn<br>245 | Ser | Thr | Met | Val | Gly<br>250 | Asn | Trp | Ala | Lys | Val<br>255 | Leu |
| Val | Val | Leu | Leu<br>260 | Leu | Phe | Ala | Gly | Val<br>265 | Asp | Ala | Glu | Thr | His<br>270 | Val | Thr |
| Gly | Gly | Ser<br>275 | Ala | Gly | His | Thr | Val<br>280 | Ser | Gly | Phe | Val | Ser<br>285 | Leu | Leu | Ala |
| Pro | Gly<br>290 | Ala | Lys | Gln | Asn | Val<br>295 | Gln | Leu | Ile | Asn | Thr<br>300 | Asn | Gly | Ser | Trp |
| His<br>305 | Leu | Asn | Ser | Thr | Ala<br>310 | Leu | Asn | Cys | Asn | Asp<br>315 | Ser | Leu | Asn | Thr | Gly<br>320 |
| Trp | Leu | Ala | Gly | Leu<br>325 | Phe | Tyr | His | His | Lys<br>330 | Phe | Asn | Ser | Ser | Gly<br>335 | Cys |
| Pro | Glu | Arg | Leu<br>340 | Ala | Ser | Cys | Arg | Pro<br>345 | Leu | Thr | Asp | Phe | Asp<br>350 | Gln | Gly |
| Trp | Gly | Gln<br>355 | Ile | Ser | Tyr | Ala | Asn<br>360 | Gly | Ser | Gly | Pro | Asp<br>365 | Gln | Arg | Pro |
| Tyr | Cys<br>370 | Trp | His | Tyr | Pro | Pro<br>375 | Lys | Pro | Cys | Gly | Ile<br>380 | Val | Pro | Ala | Lys |
| Ser<br>385 | Val | Cys | Gly | Pro | Val<br>390 | Tyr | Cys | Phe | Thr | Pro<br>395 | Ser | Pro | Val | Val | Val<br>400 |
| Gly | Thr | Thr | Asp | Arg<br>405 | Ser | Gly | Ala | Pro | Thr<br>410 | Tyr | Ser | Trp | Gly | Glu<br>415 | Asn |
| Asp | Thr | Asp | Val<br>420 | Phe | Val | Leu | Asn | Asn<br>425 | Thr | Arg | Pro | Pro | Leu<br>430 | Gly | Asn |
| Trp | Phe | Gly<br>435 | Cys | Thr | Trp | Met | Asn<br>440 | Ser | Thr | Gly | Phe | Thr<br>445 | Lys | Val | Cys |
| Gly | Ala<br>450 | Pro | Pro | Cys | Val | Ile<br>455 | Gly | Gly | Ala | Gly | Asn<br>460 | Asn | Thr | Leu |

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide (xi) SEQUENCE DESCRIPTION: SEQ ID NO:10:

Gly Asp Arg Cys Asp Leu Glu
1               5

MONOCLONAL ANTIBODIES TO PUTATIVE HCV E2/NS1 PROTEINS AND METHODS FOR USING SAME

This application is a continuation-in-part of U.S. patent application Ser. Nos. 07/456,162 and 07/610,180, both abandoned, entitled HEPATITIS C ASSAY, 7hich enjoy common ownership and are incorporated herein by reference.

BACKGROUND OF THE INVENTION

This invention relates generally to antibodies which specifically bind to hepatitis C virus (HCV), and more specifically, relates to a panel of novel hybridoma cells lines 7hich secrete monoclonal antibodies which specifically bind to the putative HCV protein E2/NS1, and methods for using these monoclonal antibodies.

Descriptions of hepatitis diseases causing jaundice and icterus have been known to man since antiquity. Viral hepatitis is now known to include a group of viral agents 7ith distinctive viral organization protein structure and mode of replication, causing hepatitis with different degrees of severity of hepatic damage through different routes of transmission. Acute viral hepatitis is clinically diagnosed by well-defined patient symptoms including jaundice, hepatic tenderness and an elevated level of liver transaminases such as aspartate transaminase and alanine transaminase.

Serological assays currently are employed to further distinguish between hepatitis-A and hepatitis-B. Non-A non-B Hepatitis (NANBH) is a term first used in 1975 that described cases of post-transfusion hepatitis not caused by either hepatitis A virus or hepatitis B virus. Feinstone et al., *New Engl. J. Med.* 292: 454-457 (1975). The diagnosis of NANBH has been made primarily by means of exclusion on the basis of serological analysis for the presence of hepatitis A and hepatitis B. NANBH is responsible for about 90% of the cases of post-transfusion hepatitis. Hollinger et al. in N. R. Rose et al., eds., *Manual of Clinical Immunology*, American Society for Microbiology, Washington, D.C., 558-572 (1986).

Attempts to identify the NANBH virus by virtue of genomic similarity to one of the known hepatitis viruses have failed thus far, suggesting that ANBH virus has a distinctive genomic organization and structure. F/wler et al., *J. Med. Virol,* 12: 205-213 (1983), and Weiner et al., *J. Med. Virol,* 21: 239-247 (1987). Progress in developing assays to detect antibodies specific for NANBH has been hampered by difficulties encountered in identifying antigens associated with the virus. Wands et al., U.S. Pat. No. 4,870,076; Wands et al., *Proc. Natl. Acad. Sci.* 83: 6608-6612 (1986); Ohori et al., *J. Med. Virol.* 12: 161-178 (1983); Bradley et al., *Proc. Natl. Acad. Sci.* 84: 6277-6281 (1987); Akatsuka et al., *J. Med. Virol.* 20: 43-56 (1986).

In May of 1988, a collaborative effort of Chiron C/rporation 7ith the Centers for Disease C/ntrol resulted in the identification of a putative NANB agent, hepatitis C virus (HCV). M. Houghton et al. cloned and expressed in *E. coli* a NANB agent obtained from the infectious plasma of a chimp. Kuo et al., Science 244: 359-361 (1989); Choo et al., Science 244: 362-364 (1989). cDNA (copy DNA) sequences from HCV 7ere identified 7hich encode antigens that react immunologically with antibodies present in a majority of the patients clinically diagnosed with NANBH. Based on the information available and on the molecular structure of HCV, the genetic makeup of the virus consists of single stranded linear RNA (positive strand) of molecular 7eight approximately 9.5 kb, and possessing one continuous translational open reading frame. J. A. Cuthbert, *Amer. J. Med. Sci.* 299: 346-355 (1990). It is a small enveloped virus resembling the Flaviviruses. Investigators have made attempts to identify the NANB agent by ultrastructural changes in hepatocytes in infected individuals. H. Gupta, Liver 8: 111-115 (1988); D. W. Bradley *J. Virol. Methods* 10: 307-319 (1985). Similar ultrastructural changes in hepatocytes as well as PCR amplified HCV RNA sequences have been detected in NANBH patients as 7ell as in chimps experimentally infected 7ith infectious HCV plasma. T. Shimizu et al., *Proc. Natl. Acad. Sci.* 87: 6441-6444 (1990).

C/nsiderable serological evidence has been found to implicate HCV as the etiological agent for post-transfusion NANBH. H. Alter et al., . *Eng. J. Med.* 321: 1494-1500 (1989); Estaben et al., *The Lancet*: August 5: 294-296 (1989); C. Van Der Poel et al., *The Lancet* August 5: 297-298 (1989); G. Sbolli, *J. Med. Virol.* 30: 230-232 (1990); M. Makris et al., *The Lancet* 335: 1117-1119 (1990). Although the detection of HCV antibodies eliminates 70 to 80% of NANBH infected blood from the blood supply system, the antibodies apparently are readily detected during the chronic state of the disease, 7hile only 60% of the samples from the acute NANBH stage are HCV antibody positive. H. Alter et al., *New Eng. J. Med.* 321: 1994-1500 (1989). These data clearly indicated the need for the identification of additional HCV proteins for efficient serodiagnosis of HCV infection. F/llowing the cloning and expression of structural protein CORE and 33C, second generation antibody assays have been developed 7hich employ HCV CORE and 33C proteins in addition to C-100 for the detection of antibodies to HCV in NANB patients. Although the second generation assays have significantly increased the sensitivity of detection, the prolonged interval between exposure to HCV and antibody detection, and the lack of adequate information regarding the profile of immune response to various structural and non-structural proteins raises questions regarding the infectious state of the patient in the antibody negative phase during NANBH infection. Therefore, there is a need for the development of assay systems to identify acute infection to HCV and the presence of HCV.

SUMMARY OF THE INVENTION

The present invention provides a panel of highly specific and novel monoclonal antibodies that can be employed for the detection of putative HCV E2/NS1 antigens. The monoclonal antibodies specifically bind to protein sequences derived from the putative HCV E2/NS1 gene. The hybridomas which produce these monoclonal antibodies are identified as follows: hybridoma H13C113 (A.T.C.C. deposit No. HB 10856) and hybridoma H23C163 (A.T.C.C. deposit No. HB 10857).

The specificity of these monoclonal antibodies enables the advantageous identification of HCV antigen in the putative E2/NS1 region, which identification can be useful in differentiation studies as 7ell as in the diagnosis and evaluation of HCV (NANB) infections.

In a preferred assay format, a test sample 7hich may contain HCV antigens is contacted with a solid phase to which a polyclonal or a monoclonal anti-HCV E2/NS1 antibody or a fragment thereof has been bound, 4o form a mixture. This mixture is incubated for a time and under conditions sufficient for antigen/antibody complexes to form. The so-formed complexes then are contacted with an indicator reagent comprising a monoclonal or polyclonal antibody or a fragment thereof, specific for the HCV antigen attached to a signal generating compound to form a second mixture. This second mixture is reacted for a time and under conditions sufficient to form antibody/antigen/antibody complexes. The presence of HCV antigen is determined by detecting the measurable signal generated. The amount of HCV present in the test sample, thus the amount of HCV antigen captured on the solid phase, is proportional to the amount of signal generated.

Alternatively, an indicator reagent comprising a monoclonal or polyclonal antibody, or fragment thereof, specific for HCV E2/NS1 antigen and a signal generating compound is added to a polyclonal or monoclonal anti-HCV antibody or fragment thereof coated on a solid phase and the test sample, to form a mixture. This mixture is incubated for a time and under conditions sufficient to form antibody/antigen/antibody complexes. The presence and amount of HCV present in the test sample, and thus the amount of HCV antigen captured on the solid phase, is determined by detecting the measurable signal. The amount of HCV present in the test sample is proportional to the amount of signal generated.

In another alternate assay format, one or a combination of more than one monoclonal antibody of the invention can be employed as a competitive probe for the detection of antibodies to HCV E2/NS1 antigen. F/r example, HCV E2/NS1 antigens, either alone or in combination, can be coated on a solid phase. A test sample suspected of containing antibody to HCV E2/NS1 antigen 4hen is incubated with an indicator reagent comprising a signal generating compound and a monoclonal antibody of the invention for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative NANBH test sample would indicate the presence of anti-HCV E2/NS1 antibody in the test sample.

In yet another assay format, a test sample is contacted with a solid phase to 7hich HCV E2/NS1 proteins are attached and an indicator reagent comprising a monoclonal antibody or fragment thereof specific for HCV E2/NS1 attached to a signal generating compound, to form a mixture. The mixture is incubated for a time and under conditions sufficient for antibody/antigen complexes to form. The presence of anti-HCV present in the test sample is determined by detecting the measurable signal generated, and comparing the signal to the measured signal generated from a known negative sample. A measurable reduction of signal of the test sample, compared to the known negative sample's signal, is indicative of the presence of anti-HCV antibodies. C/mpetitive assays for the detection of anti-HCV antibody using antigens free in solution also can be performed.

The presence of HCV E2/NS1 antigen can be detected in a tissue sample by contacting the tissue sample with an indicator reagent comprising a signal generating compound attached to a monoclonal antibody 7hich specifically binds to HCV E2/NS1 antigen or fragment thereof, to form a mixture. This mixture is incubated for a time and under conditions sufficient for antigen/antibody complex to form. The presence of HCV E2/NS1 antigen present in the tissue sample is determined by detecting the signal generated.

Also provided are kits useful for determining the presence of HCV NS1 antigen or antibody in test samples that include the monoclonal antibodies of the invention.

DETAILED DESCRIPTION OF THE INVENTION

Figure 1:
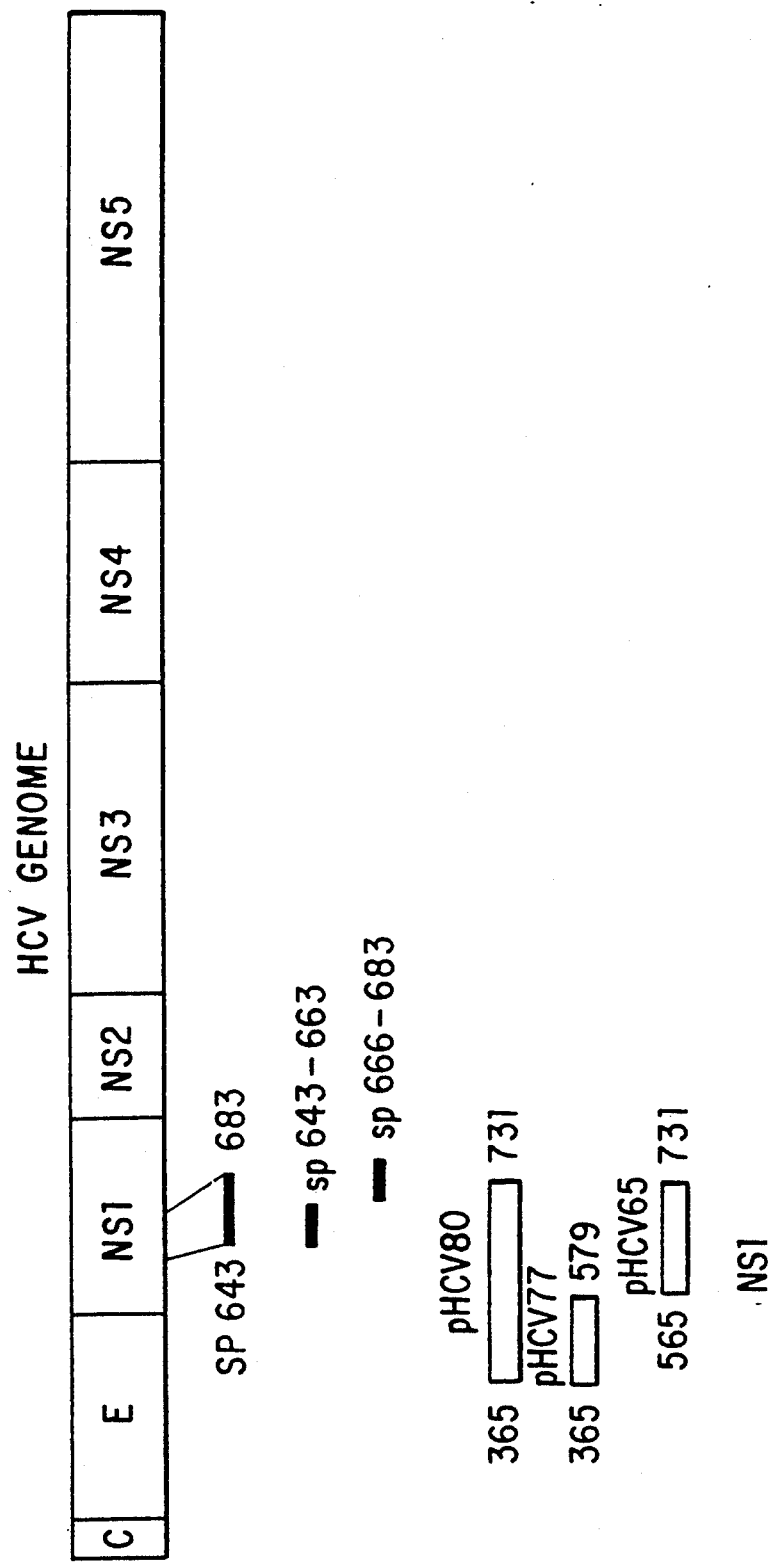
FIG. 1 is an illustration of the location of the recombinant HCV proteins on the HCV genome employed either as immunogens for the generation of monoclonal antibodies or for their characterization.

The present invention provides novel monoclonal antibodies to the putative HCV E2/NS1 protein, methods for using the monoclonal antibodies, and kits 7hich contain these monoclonal antibodies.

The monoclonal antibodies of the present invention can be employed in various assay systems to determine the presence, if any, of HCV E2/NS1 proteins in a test sample. Fragments of these monoclonal antibodies provided also may be used. F/r example, in a first assay format, a polyclonal or monoclonal anti-HCV E2/NS1 antibody or fragment thereof, or a combination of these antibodies, 7hich has been coated on a solid phase, is contacted 7ith a test sample 7hich may contain HCV E2/NS1 proteins, to form a mixture. This mixture is incubated for a time and under conditions sufficient to form antigen/antibody complexes. Then, an indicator reagent comprising a monoclonal or a polyclonal antibody or a fragment thereof, 7hich specifically binds to the HCV E2/NS1 region, or a combination of these antibodies, to which a signal generating compound has been attached, is contacted 7ith the antigen/antibody complexes to form a second mixture. This second mixture then in incubated for a time and under conditions sufficient to form antibody/antigen/antibody complexes. The presence of HCV E2/NS1 antigen present in the test sample and captured on the solid phase, if any, is determined by detecting the measurable signal generated by the signal generating compound. The amount of HCV E2/NS1 antigen present in the test sample is proportional to the signal generated.

Alternatively, a polyclonal or monoclonal anti-HCV E2/NS1 antibody or fragment thereof, or a combination of these antibodies 7hich is bound to a solid support, the test sample and an indicator reagent comprising a monoclonal or polyclonal antibody or fragments thereof, which specifically binds to HCV E2/NS1 antigen, or a combination of these antibodies to 7hich a signal generating compound is attached, are contacted to form a mixture. This mixture is incubated for a time and under conditions sufficient to form antibody/antigen/antibody complexes. The presence, if any, of HCV E2/NS1 proteins present in the test sample and captured on the solid phase is determined by detecting the measurable signal generated by the signal generating compound. The amount of HCV proteins present in the test sample is proportional to the signal generated.

In another alternate assay format, one or a combination of one or more monoclonal antibodies of the invention can be employed as a competitive probe for the detection of antibodies to HCV protein. For example, HCV proteins, either alone or in combination, can be coated on a solid phase. A test sample suspected of containing antibody to HCV E2/NS1 antigen then is incubated with an indicator reagent comprising a signal generating compound and at least one monoclonal antibody of the invention for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative ANBH test sample indicates the presence of anti-HCV E2/NS1 antibody in the test sample.

In yet another detection method, each of the monoclonal antibodies of the present invention can be employed in the detection of HCV antigens in fixed tissue sections, as well as fixed cells by immunohistochemical analysis.

In addition, these monoclonal antibodies can be bound to matrices similar to CNBr-activated Sepharose and used for the affinity purification of specific HCV proteins from cell cultures, or biological tissues such as blood and liver.

The monoclonal antibodies of the invention can also be used for the generation of chimeric antibodies for therapeutic use, or other similar applications.

The monoclonal antibodies or fragments thereof can be provided individually to detect HCV E2/NS1 antigens. It is contemplated that combinations of the monoclonal antibodies (and fragments thereof) provided herein also may be used together as components in a mixture or "cocktail" of at least one anti-HCV E2/NS1 antibody of the invention with antibodies to other HCV regions, each having different binding specificities. Thus, this cocktail can include the monoclonal antibodies of the invention which are directed to HCV E2/NS1 proteins and other monoclonal antibodies to other antigenic determinants of the HCV genome. Examples of other monoclonal antibodies useful for these contemplated cocktails include those to HCV C-100, HCV 33C, HCV CORE, HCV NS5 and/or HCV putative ENV, which are disclosed in, for example, U.S. Ser. No. 07/610,175 entitled MONOCLONAL ANTIBODIES TO HEPATITIS C VIRUS AND METHOD FOR USING SAME, U.S.S.N. 07/610,175 entitled MONOCLONAL ANTIBODIES TO HCV 33C PROTEINS AND METHODS FOR USING SAME, U.S. Ser. No. 07/648,475 entitled MONOCLONAL ANTIBODIES TO PUTATIVE HCV ENVELOPE REGION AND METHODS FOR USING SAME, U.S. Ser. No. 07/648,473 entitled MONOCLONAL ANTIBODIES TO HCV CORE PROTEINS AND METHODS FOR USING SAME and in co-filed patent application entitled MONOCLONAL ANTIBODIES TO HCV NS5 PROTEIN AND METHODS FOR USING SAME, U.S. Ser. No. 07/748,563, all of which enjoy common ownership and are incorporated herein by reference. This cocktail of monoclonal antibodies as described herein would be used in the assay formats detailed herein in place of the monoclonal antibody to HCV E2/NS1, and thus would be able to detect the E2/NS1 and other HCV antigens.

The polyclonal antibody or fragment thereof which can be used in the assay formats should specifically bind to HCV putative E2/NS1 region or other HCV proteins used in the assay, such as HCV C-100 protein, HCV 33C protein, HCV CORE, HCV ENV or HCV NS5 protein. The polyclonal antibody used preferably is of mammalian origin; human, goat, rabbit or sheep anti-HCV polyclonal antibody can be used. Most preferably, the polyclonal antibody is rabbit polyclonal anti-HCV antibody. The polyclonal antibodies used in the assays can be used either alone or as a cocktail of polyclonal antibodies. Since the cocktails used in the assay formats are comprised of either monoclonal antibodies or polyclonal antibodies having different HCV specificity, they would be useful for diagnosis, evaluation and prognosis of HCV infection, as well as for studying HCV protein differentiation and specificity.

Test samples which can be tested by the methods of the present invention described herein include human and animal body fluids such as whole blood, serum, plasma, cerebrospinal fluid, urine, biological fluids such as cell culture supernatants, fixed tissue specimens and fixed cell specimens.

The "solid phase" is not critical and can be selected by one skilled in the art. Thus, latex particles, microparticles, magnetic or non-magnetic beads, membranes, plastic tubes, walls of microtiter wells, glass or silicon chips and sheep red blood cells are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers;

natural polymers containing nitrogen, such as proteins and derivatives, including cross-linked or modified gelatins;

natural hydrocarbon polymers, such as latex and rubber;

synthetic polymers 7hich may be prepared 7ith suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides;

porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters 7ith the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and absorption qualities for a 7ide variety of reagents including monoclonal antibodies. Nylon also possesses similar characteristics and also is suitable.

It is contemplated that such porous solid supports described hereinabove are preferably in the form of sheets of thickness from about 0.01 to 0.5 mm, preferably about 0.1 mm. The pore size may vary within 7ide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. pa.ent application Ser. No. 227,272.

The indicator reagent comprises a signal generating compound (label) which is capable of generating a measurable signal detectable by external means conjugated (attached) to a specific binding member for HCV. "Specific binding member" as used herein means a member of a specific binding pair. That is, two different molecules 7here one of the molecules through chemical or physical means specifically binds to the second molecule. In addition to being an antibody member of a specific binding pair for HCV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HCV as in a sandwich assay, to the capture reagent as in a competitive assay, or to the ancillary specific binding member as in an indirect assay.

The various signal generating compounds (labels) contemplated include chromogens, catalysts such as enzymes, luminescent compounds such as fluorescein and rhodamine, chemiluminescent compounds such as acridinium, phenanthridinium and dioxetane compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction 7ith one or more additional substances.

Other embodiments which utilize various other solid phases also are contemplated and are within the scope of this invention. F/r example, ion capture procedures for immobilizing an immobilizable reaction complex with a negatively charged polymer, described in copending U.S. patent application Ser. No. 150,278 corresponding to EP publication 0326100, and U.S. patent application Ser. No. 375,029 (EP publication no. 0406473) both of which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in copending U.S. patent application Ser. No. 921,979 corresponding to EPO Publication No. 0 273,115, which enjoys common ownership and 7hich is incorporated herein by reference.

Also, the methods of the present invention can be adapted for use in systems 7hich utilize microparticle technology including in automated and semi-automated systems wherein the solid phase comprises a microparticle. Such systems include those described in pending U.S. patent application Ser. Nos. 425,651 and 425,643, which correspond to published EPO applications Nos. EP 0 425 633 and EP 0 424 634, respectively, 7hich are incorporated herein by reference.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunnelling microscopy eliminates the need for labels 7hich normally must be utilized in many immunoassay systems to detect antigen/antibody complexes. Such a system is described in pending U.S. patent application Ser. No. 662,147, 7hich enjoys common ownership and is incorporated herein by reference.

The use of SPM to monitor specific binding reactions can occur in many ways. In one embodiment, one member of a specific binding partner (the analyte specific substance, which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis(succinimidyl) suberate, SPPD (succinimidyl 3-[2-pyridyldithio] propionate), SMCC (succinimidyl-4-[N-maleimidomethyl] cyclohexane-1-carboxylate), SIAB (succinimidyl [4-iodoacetyl] aminobenzoate), and SMPB (succinimidyl 4-[1-maleimidophenyl] butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent application Ser. Nos. 150,278, filed Jan. 29, 1988, and Ser. No. 375,029, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the monoclonal antibodies of the present invention can be utilized in non-solid phase assay systems. These assay systems are known to those skilled in the art, and are considered to be within the scope of the present invention.

It is contemplated that the reagent employed for the assay can be provided in the form of a kit with one or more containers such as vials or bottles, with each container containing a separate reagent such as a monoclonal antibody, or a cocktail of monoclonal antibodies, detection reagents and washing reagents employed in the assay.

The following examples demonstrate the advantages and utility of this invention for serodiagnosis of HCV by describing methods for the development, characterization, epitope mapping and clinical utility of these monoclonal antibodies. The methods used for monoclonal antibody development follow procedures known in the art and detailed in Kohler and Milstein, *Nature* 256: 494 (1975) and reviewed in J. G. R. Hurrel, ed., Monoclonal Hybridoma Antibodies: Techniques and Applications, CRC Press, Inc., Boca Raton, Fla. (1982). Another method of monoclonal antibody development which is based on the Kohler and Milstein method is that of L. T. Mimms et al., *Virology* 176: 604–619 (1990), which is incorporated herein by reference. These examples are meant to illustrate, but not to limit, the spirit and scope of the invention.

EXAMPLES

EXAMPLE 1

Immunization of Mice with SEQ. ID. No. 6 Selection of Synthetic Peptide for Generation of Monoclonal Antibodies to HCV E2/NS1 Region Immunogenic domains of E2/NS1 region of HCV genome encompassing a.a. 600–720 (SEQ. ID. NO. 1) were mapped with PEPSCAN analysis. A PEPSCAN kit was purchased from Cambridge Research Bioscience (Valley Stream, N.Y., U.S.A.) to synthesize a series of overlapping hexamer peptides (overlap of five amino acids) encompassing HCV a.a. 600–720 (SEQ. ID. NO. 1), on derivitized polypropylene pins supplied by the manufacturer. The synthesis protocol supplied with the kit was followed exactly for the synthesis of these peptides. Briefly, the polypropylene pins which contained the F-moc $\beta$-alanine as the end group amino acid were deprotected with 20% (v/v) piperidine in dimethylformamide (DMF) for 30 min. Pins were washed with DMF (1×5 min.), Methanol (4×2 min.) followed by a final DMF wash (1×5 min.). F-moc active esters of amino acids were prepared at 30 mM concentration in 1-hydroxybenzotriazole (HOBt) in DMF. Amino acids were dispensed (175 ul) in wells of 96 well microtiter plates supplied with the kit in desired sequence, starting at the carboxy terminus. Deprotected pins were lowered in the amino acid solutions and incubated at room temperature (RT) overnight. Following the DMF methanol wash sequence as described above, the deprotection, washing and coupling steps were repeated until all amino acid in each of the peptides sequence were coupled. After a final deprotection step, the terminal amino acids were acetylated by incubating the pins with DMF:acetic anhydride:triethylamine at 5:2:1 (v/v/v) for 90 min. at RT. Following the DMF/methanol wash sequence, pins were air dried. Before the serological analysis, the final side chain deprotection and neutralization was accomplished by treating the pins with Trifluoroacetic acid:Phenol:Ethanedithiol at 95:2.5:2.5 (v/w/v). Pins were washed with dichloromethane (2×2 min.), 5% diisopropylethylamine/dichloromethane (1×5 min.) and dichloromethane (1×5 min.). Finally, pins were air dried, washed with water, soaked in methanol for 18 hrs., dried and stored dessicated in refrigerator.

FAB dimers of IgG purified from sera of individuals seropositive for antibodies to HCV proteins were used as the primary antibody for the serological analysis of these peptides using the EIA procedure recommended by the manufacturer. Briefly, the primary antibody was diluted to appropriate concentration in phosphate buffered saline (PBS) containing 0.1% Tween-20® (Bio-Rad, Richmond, Calif.), 1% ovalbumin (available from Sigma, St. Louis, Mo.), and 1% bovine serum albumin (available from Sigma). Peptide pins were incubated with the primary antibody overnight at 4° C. Following several washes with PBS/Tween-20®, pins were incubated with appropriately diluted goat anti-mouse HRPO for 1 hr. at room temperature. Azido-di-3-ethylbenzthiazodinsulphonate dissolved in a phosphate-citrate buffer containing hydrogen peroxide was used as the color developing reagent. The optical density of the color developed was measured at 405 nm after incubation of the pins with the developing reagent for 15-20 min. Based on the reactivity of these sera in EIA, four amino acid sequences (a.a. 607-627 (SEQ. ID. No. 2), a.a. 643-663 (SEQ. ID. No. 3), a.a. 666-683 (SEQ. ID. No. 4) and a.a. 671-691 (SEQ. ID. NO. 5 were identified as the immunogenic domains as disclosed in U.S. patent application Ser. No. 610,180 previously incorporated herein by reference. Each of these four sequences and an additional sequence, which was the combination of the two most immunogenic sequences (a.a. 643-683) (SEQ. ID. No. 6) were synthesized by a stepwise solid phase synthesis starting at the carboxy terminus by a procedure similar to that described in E. Gross and T. Heinhofer, eds. Barany and Merrifield, *The Peptides* 2: 1284, Academic Press, New York, N.Y. Based on the EIA reactivity of a panel of HCV positive sera as disclosed in the U.S. patent application Ser. No. 610,180 previously incorporated herein by reference, peptide 643-683 (SEQ. ID. NO. 6) was chosen as the immunogen for the generation of monoclonal antibodies to HCV NS1. FIG. 1 shows the location of these peptides on the HCV genome.

Immunization of Mice

Female Balb/c were immunized with approximately 50 ug of the crude peptide 643-683 (HCV a.a. 643-683, SEQ. ID. NO. 6) using the RIBI adjuvant system (RIBI Immunochemicals Res., U.S.A.). On day one, mice received 50 ug of the peptide with 50 ug each of Trehalose dimycolate (TDM) and M. Phlei in a buffer emulsion prepared according to the manufacturer's instructions. Subsequent immunizations were done on day 18, 34, 42 and 63. Mice were bled on day 25 and 77, and the immune response was assessed by EIA using microtiter plates coated with the immunogen. Mice were allowed to rest for at least eight weeks before the fusion.

Enzyme-Linked Immunoassay (EIA)

The immune response to the immunizing antigen was assessed by microtiter EIA. Wells of microtiter plates were coated with 100 µl of purified synthetic peptide (a.a. 643-683, SEQ. ID. O. 6) on 0.1M bicarbonate buffer at pH 9.5. After washing with Phosphate Buffered Saline (PBS) which also contained 0.01% sodium dodecyl sulfate (SDS) and 0.05% Tween-20® (available from Bio-Rad Laboratories, Richmond, Calif.) free sites were overcoated with 1% BSA in bicarbonate buffer at pH 9.5. Plates were stored at 4° C. following a final wash. Sera from native or immunized mice were serially diluted in 100 µl of dilution buffer which contained 20 mM sodium phosphate, pH 7.4, 0.15M NaCl, 20% normal goat serum, 10% fetal calf serum, 5 mM EDTA, 10 mM EGTA, 50 mM Tris, 0.2% Tween-20® with sodium azide as a preservative (at pH 6.8). The diluted sera were reacted with the antigen for three (3) hours at 37° C. The plates were washed and 100 µl of appropriately diluted goat anti-mouse IgG (heavy [h] and light [l] chain) Horseradish Peroxidase (HRPO)-conjugated antibody (Jackson Immunochemicals, West Grove, Pa.) was added. The plates were incubated at 37° C. for two (2) hours. After a final wash, 100 µl of o-phenylenediamine:2 HCL (OPD) color reagent was added. The reaction was carried out at room temperature for 10 to 30 minutes, and then stopped by the addition of 1 ml of 1N $H_2SO_4$. The absorbance at 492/600 nm was recorded, which was found to be directly proportional to the amount of specific antibody bound to the antigen.

EXAMPLE 2

Cell Fusion

Upon demonstration of specific anti-HCV antibody present at reasonable titers in sera of immunized mice, the mice were allowed to rest for at least eight weeks prior to a pre-fusion boost of antigen. The pre-fusion antigen boost then was performed by intravenous (IV) tail vein injection of approximately 40 µg of respective purified HCV synthetic peptide (SEQ. ID. NO. 6). Three days later the mice were sacrificed, and their spleens which contained anti-HCV antibody-producing cells were disrupted into single cells. These single cell suspensions were treated with 0.83% $NH_4Cl$ to remove red blood cells, and then these suspensions were mixed with SP2/0 cells at a 10:1 (SP2/0:spleen cells) ratio. The mixed cells were centrifuged, washed once with serum-free medium, and again centrifuged. The fusogen polyethylene glycol (PEG) was used to form hybrids of the immune donor spleen cells with the myeloma cell line SP2/0 (HRPT neg.). Kohler and Milstein, *Nature* 356:494 (1975), and reviewed in J. G. R. Hurrel, ed., *Monoclonal Hybridoma Antibodies: Techniques and Applications*, CRC Press, Inc., Boca Raton, Fla. (1982). Briefly, fusion of the spleen and SP2/0 cells was accomplished by exposing the pellet to 40% PEG (ATCC, mw 1300-1600) In serum-free Iscoe's Modified Dulbecco's Medium (IMDM) for two minutes. The PEG and cell suspension was diluted slowly by the addition of 20 ml of serum-free IMDM over a period of five minutes, followed by collection of the cells by centrifugation. The supernatant was decanted and replaced with 30 ml IMDM containing 20% fetal bovine serum (FBS) (Hyclone Laboratories, Logan, Utah) with HAT (hypoxanthine, aminopterin and thymidine) media in order to select for hybridomas. Spleen cells from one non-immune BABB/c mouse also were added as a feeder layer. The cells were plated at 0.1 ml/well in three 96-well tissue culture plates. An additional 0.1 ml of HAT media was added to each well three days later. At weekly intervals thereafter, one-half the media was replaced with IMDM containing 20% FBS with HT (hypoxanthine and thymidine), and hybrids were allowed to grow for an additional seven to fourteen days.

It was found that some of the hybrids were composed of spleen cells making antibody to HCV fused with SP2/0 cells. Briefly, the fusogen promoted fusion of spleen cell and SP2/0 cell membranes, which formed a heterokaryon containing nuclei of both cells. Eventually, the dissimilar nuclei fuse produced a single nucleus capable of synchronous mitosis. As the fused cells divided, the hybrid stabilized by losing chromosomes of each nucleus. The fused cells were plated into multiple 96-well plates at $10^5$ to $10^6$ cells per well. The hybrid cells formed from SP2/0:spleen cell fusions were selectively propagated by culturing in HAT medium. All unused SP2/0 or SP2/0:SP2/0 &used cells were prevented from growing aminopterin, and unfused spleen cells on spleen:spleen fused cells died off in culture. Only SP2/0:spleen cell hybrids grew in the HAT selective medium.

EXAMPLE 3

Screening and Cloning of Monoclonal Antibodies

After 10 to 14 days, culture fluids from wells containing hybridoma cell growth were screened for the presence of a monospecific antibody as follows. Each of the hybridoma supernatants from the NS1 fusions were tested by the EIA procedure described in Example 1 with the synthetic peptide a.a. 643-683 (SEQ. ID. O. 6) coated on the solid phase. Hybridoma culture fluids reacting specifically to the immunogen, i.e., HCV protein SEQ. ID. NO. 6 were selected for cloning by the limiting dilution method, using the guidelines outlines by J. W. Goding, *Monoclonal Antibodies: Principles and Practices*, Academic Press, New York (1983). Culture supernatant of cloned samples were tested again by EIA with the immunogen as described above in Example 1, for the confirmation of monospecific reactivity to HCV protein sequence. Clones with strongest reactivity specifically to the synthetic peptide were selected for expansion and further analysis.

EXAMPLE 4

Amplification of Antibody Yields by Ascites Method

In order to obtain greater amounts of monoclonal antibodies, 10 to 20 million cloned cells of the desired hybridoma cell line were inoculated into a BALB/c mouse previously treated i.p. with 0.5 ml pristane (2,6,10,14-tetramethylpentadecane) by the method outlined in J. G. R. Hurrel, ed., *Monoclonal Hybridoma Antibodies: Techniques and Applications*, CRC Press, Inc., Boca Raton, Fla. (1982). Pristane treatment enhanced growth of mouse myeloma hybrids within the peritoneum of the mouse, and the ascites fluids which formed were rich in the monoclonal antibody secreted by the hybrid cells. After formation of adequate ascites fluid (approximately seven days), the mice were sacrificed and the ascites were withdrawn from the peritoneum, clarified by centrifugation and stored at $-20°$ C. Monoclonal antibodies from ascites fluid were purified using protein-A sepharose (according to J. G. R. Hurrell ed., supra). All characterization procedures described herein were performed with either culture supernatants, ascites fluids or protein-A purified IgG.

EXAMPLE 5

Characterization of Monoclonal Antibodies EIA

Purified IgG of monoclonal antibodies were titrated on microtiter plates coated with the immunogen (peptide 643-683, SEQ, ID. NO. 6) as well as on plates coated with the purified recombinant HCV E2/NS1 protein PHCV80 (a.a. 365-731, SEQ ID NO. 7) by the EIA protocol described in Example 1. The detail description of cloning and expression of pHCV80 is described in Example 6. EIA reactivity of monoclonal antibodies of this invention to the immunogen as well as the recombinant HCV E2/NS1 protein is described in Table 1.

Western Blot Analysis

Figure 2:
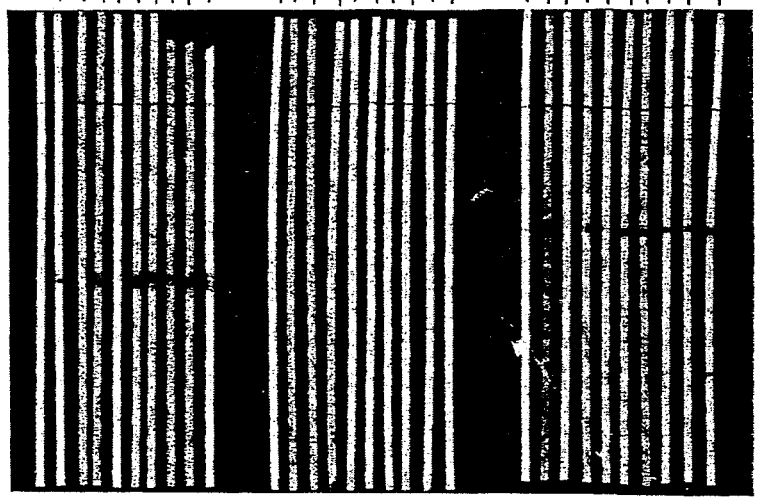
FIG. 2 is a Western blot analysis illustrating specific binding monoclonal antibodies H13C113 and H23C163 to HCV NS1.

Approximately 300 μg of the HCV protein PHCV-80 (a.a. 365-731, SEQ. ID. NO. 7) were treated with SDS and 2-mercaptoethanol at 95° C., and electrophoresed in a 12% polyacrylamide-SDS gel (Laemmli et al., Nature 227:680-685 (1970). Proteins were transferred overnight from the gel to nitrocellulose by electrophoresis at 100 mamp, or transferred in 1-2 hours at 1.0 amp, in a standard transfer buffer which comprised 25 mM Tris [(Hydroxymethyl) Aminomethane] 192 mM glycine, and 2.0% methanol, pH 8.3. (Towbin et al., *Proc. Natl. Acad. Sci.* 73:4350-4354 [1979]). After transferring the proteins and blocking the nitrocellulose with 5% dry milk in PBS, the nitrocellulose was cut into strips (each strip containing approximately 5 μg of the protein which then were used to determine the presence of anti-HCV antibody in test sera (or other samples). Reaction mixtures consisted of a nitrocellulose strip incubated with an appropriate amount of test sample in 2.0 ml of buffer (20 mM Tris, 1 mM EDTA, 0.2M NaCl, 0.3% Triton X-100 ® and 2 mg/ml bovine serum albumin (BSA), pH 7.5, 5% E. C/li lysate and 3% CKS lysate overnight at 4° C. The strips were washed with buffered detergent (10 mM phosphate buffered saline (PBS) pH 7.5, containing 0.1% SDS and 0.5% Triton X-100 ®) followed by addition of goat anti-mouse IgG antibody conjugated to HRPO. The strips were incubated for one to two hours at room temperature, followed by washing with buffered detergent. Finally, antibody bound to the protein was visualized by addition of freshly prepared HRP color reagent (Bio-Rad Laboratories, Richmond CA) (120 mg dissolved in 40 ml ice-cold methanol, then diluted into 200 ml Tris buffered saline [TBS] pH 7.8, containing 120 μl of 30% hydrogen peroxide. FIG. 2 illustrates the specific reactivity of the monoclonals of this invention to the HCV E2/NS1 protein.

Competition with Immune Human Sera

In order to establish whether each of the monoclonal antibodies recognized an epitope that is immunologic in humans, a competition assay was performed as follows. Each of the monoclonal antibodies was tested in an assay where the monoclonal antibody competed with a human sera seropositive for antibody to E2/NS1 (SEQ. ID. NO. 1) for the binding to the antigen. Briefly, a human serum from an individual infected with NANBH and strongly seropositive for antibodies to E2/NS1 protein of HCV was included in the reaction mixture with each of the monoclonal antibodies at a final concentration of 10%. Microtiter EIA was carried out as described in Example 1. A greater than 50% inhibition in the binding of the monoclonal antibody to the respective protein by the immune human sera was considered as competitive (data presented in Table 1). Monoclonal antibodies H13C113 and H23C163 were not significantly competed by sera from individuals seropositive for antibodies to HCV E2/NS1.

Isotype

The isotypes of each of the monoclonal antibodies was determined by using an isotyping kit (Amersham, Arlington Heights, Ill.) and following the instructions included with it. Briefly, the tissue culture supernatant of each monoclonal antibody and appropriate controls were reacted at a 1:5 dilution with strips coated with specific anti-isotype antibody, provided in the kit described above. Assay protocol was followed exactly according to the manufacturer's instructions. The isotype of each monoclonal antibody of the invention is provided in TABLE 1.

EXAMPLE 6

Epitope Mapping

Monoclonal antibodies generated against the synthetic peptide (SEQ. ID. NO. 6) were mapped to the specific region of the HCV E2/NS1 protein by (a) Western blot reactivity of each of the monoclonal antibodies with subfragments of the HCV E2/NS1 protein and (b) reactivity with several synthetic peptides selected for respective protein sequences, by microtiter EIA using the procedure described in Example 1.

Reactivity of Monoclonals to Various Subfragments of Recombinant HCV NS1 proteins Briefly, several individual oligonucleotides representing a.a. 365-731 of HCV genome were ligated and cloned as three separate EcoRI-BAMHI subfragments into the CKS fusion vector pJ0200. These three subfragments were designated as pHCV80 (a.a. 365-731) (SEQ. ID. NO. 7), pHCV77 (a.a. 365-579) (SEQ. ID. NO. 8), and pHCV65 (a.a. 565-731) (SEQ. ID. NO. 9), as illustrated in FIG. 2. The detailed methods for cloning and expression of the CKS-fusion proteins are as disclosed in U.S. patent application Ser. No. 07/610,180 and 07/572,822, which enjoy common ownership and are incorporated herein by reference. Cell lysates of these clones were used as antigens on Western blot analysis using the protocol described in Example 5 for preliminary epitope mapping of anti-NS1 monoclonal antibodies. FIG. 2 shows the binding of monoclonal antibodies H13C113 and H23C163 to recombinant HCV E2/NS1 protein subfragments, wherein lane1 (normal human sera), lane 2(HCV immune human sera), and lane 3(normal mouse sera) were included as controls. Lane 4 contains hybrid supernatant from which H13C113 was cloned, lane 6 contains monoclonal antibody H13C113, lane 5 contains a sister clone of monoclonal antibody H13C113 (H13C44), lane 10 contains monoclonal antibody H23C163, while lanes 8 and 9 contain sister clones of monoclonal antibody H23C163 (H23C41 and H23C41 respectively). Data for epitope mapping with these subfragments are illustrated in FIG. 2. Monoclonal antibodies H13C113 and H23C163 showed reactivity with pHCV 80 (SEQ. ID. NO. 7) and pHCV 65 (SEQ. ID. NO. 9) which indicated the reactivity with HCV a.a. 564-731 (SEQ. ID. NO. 9).

Reactivity with Synthetic Peptides

Several amino acid sequences were selected from different regions of HCV protein NS1 based on the PEPSCAN analysis as described in Example 1. A list of the peptides used for the epitope mapping of these monoclonal antibodies is listed below in TABLE 2.

TABLE 2

| | Epitope Mapping with Synthetic Peptides | | |
|---|---|---|---|
| REGION OF HCV GENOME | MONOCLONAL TESTED | PEPTIDE a.a. | REACTIVITY OF EACH WITH PEPTIDE |
| NS1 | H13C113 | sp 643-663 | sp 643-663 |
| | H23C163 | sp 643-663 sp. 666-683 | sp. 643-683 |

Each of these peptides were assembled on a resin support by a stepwise solid phase synthesis, starting with the carboxy terminal residue. A procedure was employed similar to that described in E. Gross and T. Heinehofer, eds., Barary and Merrifield, *The Peptides* 2:1284, Academic Press, New York, N.Y. (1980), using a reaction vessel of an Applied Biosystems Synthesizer Model 430A. After cleavage of the peptide from the resin, the peptide was washed with diethyl ether and extracted in 40% acetic acid solution. Crude peptide obtained after lyophilization of the aqueous solution was employed as the antigen target for epitope mapping experiments. Briefly, each of the peptides tested was coated on microtiter wells at a concentration of 10 μg/ml in bicarbonate buffer at pH 9.5. EIA was performed in the manner described in Example 1. Monoclonal antibody showing reactivity four times the negative control was considered positive.

Figure 3:
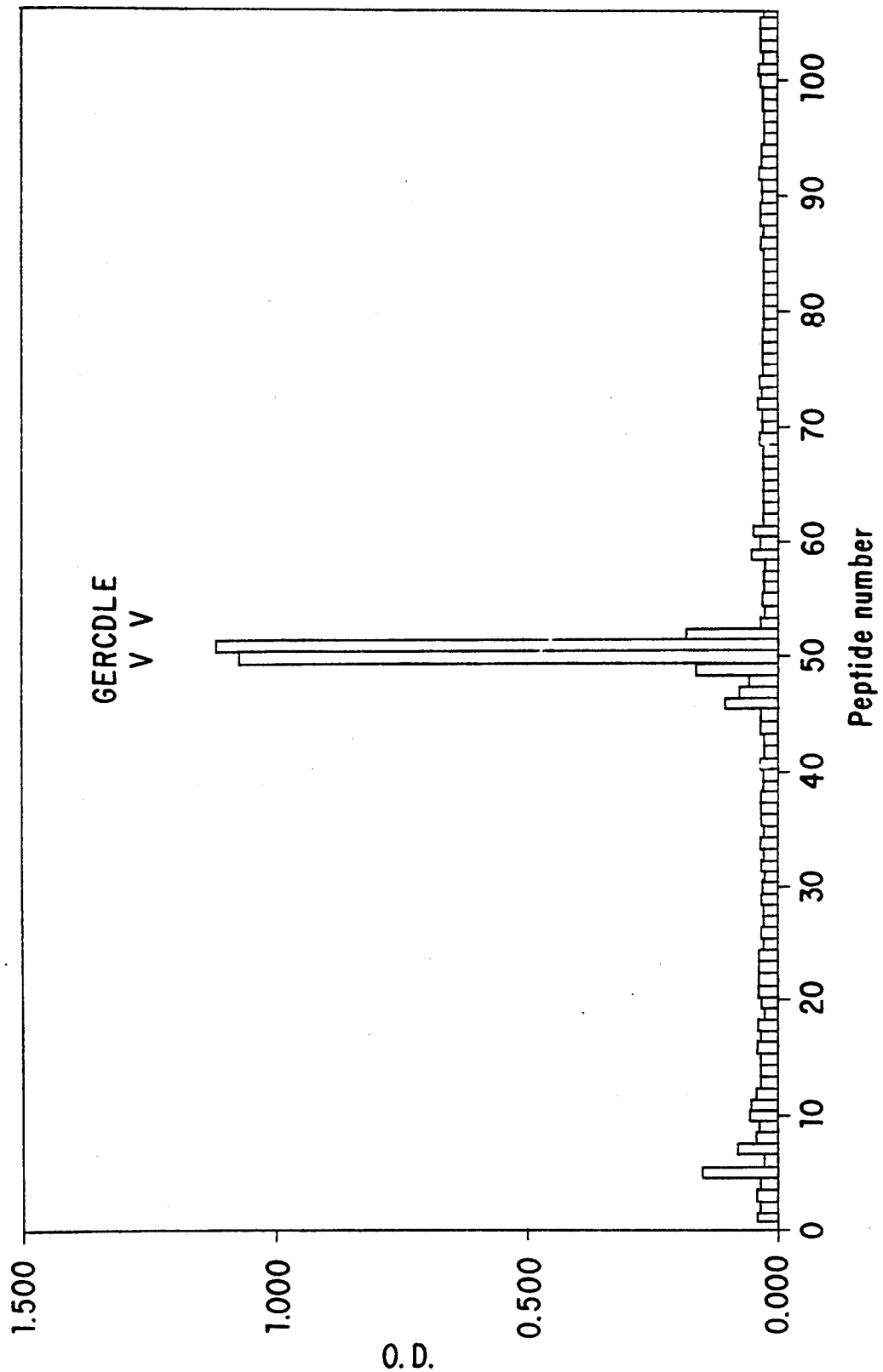
FIG. 3 is a profile of PEPSCAN analysis 7ith overlapping hexamer peptides (a.a. 600-720 of HCV) of monoclonal antibody H13C113 illustrating the epitope specificity of H13C113 to HCV a.a. 649-655.
Figure 4:
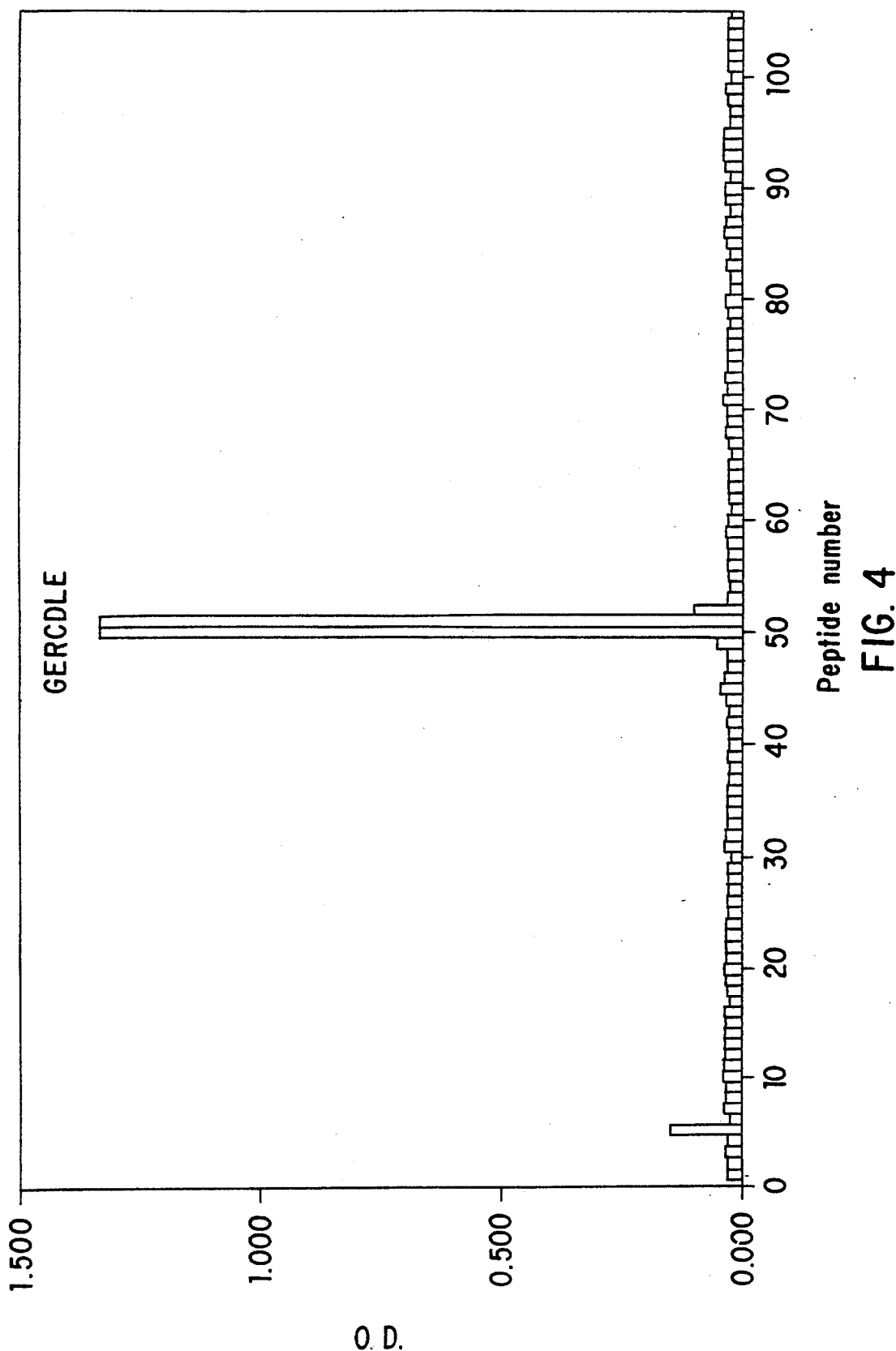
FIG. 4 is a profile of PEPSCAN analysis 7ith overlapping hexamer peptides (a.a. 600-720 of HCV) of monoclonal antibody H23C163 illustrating 4he epitope specificity of H23C163 to HCV a.a. 649-655.

In addition, monoclonal antibodies to HCV NS1 were also mapped with PEPSCAN analysis as described in Example 1. An EIA was performed with each of the monoclonal antibodies to HCV NS1 by the procedures similar to one outlined in Example 1 using the tissue culture supernatants of monoclonal antibodies as the primary antibody and goat anti-mouse HRPO as the secondary antibody with overlapping hexamer peptides encompassing a.a. 600-720 (SEQ. ID. NO. 1) of the HCV genome. Data are illustrated in FIG. 3 and FIG. 4. Monoclonal antibody H13C113 and H23C163 specifically reacted with peptide sequence GDRCDLE (a.a. 649-655) (SEQ. ID. NO. 10) of the HCV genome.

EXAMPLE 7

EIA for the Detection of HCV Proteins in Biological Samples Preparation of Rabbit Polyclonal Antibodies Against HCV E2/NS1 Region Young rabbits (3-4 months old and weighing approximately 2-3 kg) (available from Hazelton LAbs, Denver Pa.) are immunized with 100-150 μg of highly purified HCV E2/NS1 synthetic peptide or the E2/NS1 recombinant proteins cloned and expressed in either eukaryotic or prokaryotic systems as described in Example 1 in Freund's complete adjuvant by intra-muscular (i.m.) injection at four different sites. Subsequently, two immunizations are carried out at two week intervals in similar fashion in Freund's incomplete adjuvant. Immune response of the rabbits is monitored by EIA and Western blot analysis. Rabbits are bled when acceptable immune response to the protein is achieved. IgG from the immune rabbit sera is purified by Protein-A sepharose affinity chromatography, by methods known to those in the art.

Coating of Solid Phase

Rabbit IgG is prepared as herein described and then is coated on polystyrene beads as the solid support for capture of E2/NS1 antigens in test samples. The polystyrene beads are washed with distilled water and incubated at 40° C. for two hours with 5-10 μg/ml of purified HCV E2/NS1 synthetic peptide rabbit IgG in a buffer solution (0.1M Tris, 0.5M NaCl, 0.0022% Triton X-100 ®, pH 8.5). The beads are washed once with PBS and then soaked in 0.1% Triton X-100 ® in PBS for approximately one hour at 40° C. After washing twice with PBS, the beads are overcoated with 3% bovine serum albumin (BSA) in PBS for approximately one hour at 40° C. Finally, the beads are overcoated with 5% sucrose solution in PVS and dried under nitrogen. Anti-HCV human polyclonal IgG, purified from sera of individuals seropositive for HCV antibodies to E2/NS1 also is coated in similar fashion.

EIA

Monoclonal antibodies specific for HCV E2/NS1 are screened for use as the probe for detection of HCV proteins in a test sample by EIA. Briefly, each of the monoclonal antibodies is incubated with the E2/NS1 antigen in the presence of polystyrene beads coated with anti-HCV rabbit polyclonal IgG. The protocol for EIA is similar to that described hereinbelow.

200 μl of test specimen suspected of containing antigen to HCV E2/NS1 protein is incubated in a reaction tray with 50 μl of monoclonal antibody of the invention (at a final protein concentration of about 5–10 μg/ml diluted in a buffer containing 20 mM Tris, 0.1 mM NaCl, 1 mM EDTA, 3.0% BSA, 0.3% Tween-20 ® and 10% FBS at pH 7.5), and a bead coated with HCV rabbit IgG (prepared as described hereinabove). Overnight incubation at ambient room temperature is performed, and then the beads are washed with distilled water and 200 μl of appropriately diluted Horseradish Peroxidase labeled goat anti-mouse IgG (H & L) (Jackson Immunoresearch, West Grove, Pa.) is added. Incubation with the labeled probe is carried out at about 40° C. for approximately two hours. Beads are washed and transferred to reaction tubes containing 300 μl of O-phenylenediamine (OPD) color reagent. The reaction is carried out at ambient room temperature in the dark for about 30 minutes, and then it is stopped by the addition of 1 ml of 1N $H_2SO_4$. Absorbance is recorded at 492/600 nm. A negative control previously screened and confirmed to be negative for NANBH infection is included in the experiment. The positive control consists of a solution of synthetic peptide to E2/NS1 in the buffer solution described hereinabove. Triplicates of both positive and negative control are included with each set of experiments.

In order to determine the efficiency of the antigen capture assay for the detection of HCV E2/NS1 in a sample, various concentrations of recombinant HCV E2NS1 synthetic peptide, ranging from 100 ng peptide/ml to 100 pg peptide/ml are diluted in the buffer mentioned hereinabove. The EIA procedure described above is performed with each of the diluted panel members. For the purposes of comparison, each of the panel members is tested with (a) anti-HCV rabbit polyclonal antibody on the solid phase and (b) anti-HCV human polyclonal antibody on the solid phase. The efficiency of the assay then is determined by evaluating data obtained.

The hybridomas which produce the monoclonal antibodies of the invention are identified as hybridoma H13C113 producing monoclonal antibody H13C113, and hybridoma H23C163 producing monoclonal antibody H23C163. Hybridomas H13C113 and H23C163 were deposited at the American Type Culture Collection (ATCC), 12301 Parklawn Drive, Rockville, Md. 20852 as of Aug. 20, 1991, and have been accorded the following deposit numbers: hybridoma H13C113 was accorded ATCC deposit number HB 10857, and hybridoma H23C163 was accorded ATCC deposit number HB 10856.

Thus, the novel monoclonal antibodies of the invention can be used in a variety of ways. These monoclonal antibodies can be used for immunoprecipitation of amplified product and detection of HCV nucleic acid microparticles or carrier coated with anti-HCV monoclonal antibody used to capture virus or viral protein associated with HCV RNA. Then detection methodology for RNA may be used. An example of this type of assay is taught in pending U.S. patent application Ser. No. 07/568,663, entitled A METHOD FOR AMPLIFYING AND DETECTING A TARGET NUCLEIC ACID SEQUENCE, which enjoys common ownership and is incorporated herein by reference.

These monoclonal antibodies also can be used for localization of HCV antigens within the cell using HCV monoclonal antibody tagged directly (fluorescence, colloidal gold, etc.) or using secondary tagged anti-mouse antibody. Histopathology of disease may be tracked. Further, the detection of native or recombinant HCV antigens in sera, tissue, cells, culture media, or body fluid using individual monoclonal antibodies in a sandwich configuration or a cocktail of monoclonal antibodies on the solid phase and in the detection system.

One step antigen assays using monoclonal antibodies against non overlapping epitopes may also be performed. Some monoclonal antibodies may recognize antigenic epitopes not recognized by the infected individual and therefore may be possible to recognize serum Ag both free and bound with human antibody. Furthermore, "cryptic" or hidden antigens or antigenic determinants may be uncovered by treatment of specimen with detergent or reducing agent or both. For example, CORE antigen may exist in a capsid form covered by the virus envelope. Stripping the envelope with detergent should expose CORE antigen. Monoclonal antibodies may also offer pragmatic advantages over high titer polyclonal antibody in giving greater sensitivity in assay or allowing shorter incubation times.

Further, antibody immunoassays, one or two step competitive assays, were developed in which anti-HCV competed with labeled anti-HCV monoclonal antibody for binding to a limited number of antigenic sites. A more sensitive competitive assay may be developed in which human anti-HCV binds to HCV Ag in solution blocking or inhibiting the HCV Ag binding in HCV Ag sandwich assay. Competitive assays using monoclonal antibodies allow a more precise mapping of human antibody epitopes and may be useful for determining virus neutralizing antibody epitopes. Some monoclonal antibodies may have virus neutralizing activity. Finally, monoclonal antibodies should be useful in immunoaffinity purification of native viral and recombinant HCV antigens and proteins.

Other variations of applications of the use of these unique monoclonal antibodies provided herein include the detection of HCV in immune complexes, or latent and/or cryptic antigens, and/or associated with viral nucleic acid for detection of the nucleic acid by PCR, LCR, or by direct hybridization. Still other variations and modifications of the specific embodiments of the invention as set forth herein 7ill be apparent to those skilled in the art. Accordingly, the invention is intended to be limited only in accordance 7ith the appended claims.

TABLE 1

MONOCLONAL ANTIBODIES TO HCV NS1 PROTEIN

| IMMUNOGEN | MAB ID | ISOTYPE | COMP WITH IMMUNE HU.SERA | WESTERN BLOT | | TITER | | EPITOPE |
| --- | --- | --- | --- | --- | --- | --- | --- | --- |
| | | | | pHCV-65[a] | pHCV-80[b] | 643-683 | pHCV80 | HCV A.A. |
| sp 643-683 | H13C113 | IgG3,k | − | + | + | 10 ng/ml | 80 ng/ml | 649-655[c] |
| | H23C163 | IgG2b,k | − | + | + | 80 ng/ml | 1 ug/ml | 649-655 |

[a] pHCV-65 a.a. 565-731
[b] pHCV-80 a.a. 365-731
[c] a.a. sequence = Gly—Glu—Arg—Cys—Asp—Leu—Glu

---

We claim:

1. A monoclonal antibody which specifically binds to Hepatitis C Virus (HCV) E2/NS1 antigen, wherein said monoclonal antibody is the monoclonal antibody secreted by hybridoma cell line ATCC deposit No. HB 10856.

2. A monoclonal antibody which specifically binds to Hepatitis C Virus (HCV) E2/NS1 antigen, 7herein said monoclonal antibody is the monoclonal antibody secreted by hybridoma cell line ATCC deposit No. HB 10857.

3. A hybridoma cell line which secretes a monoclonal antibody which specifically binds to Hepatitis C Virus (HCV) E2/NS1 antigen and 7herein said hybridoma cell line is A.T.C.C. deposit No. HB 10856.

4. A hybridoma cell line 7hich secretes a monoclonal antibody which specifically binds to Hepatitis C Virus (HCV) E2/NS1 antigen and wherein said hybridoma cell line is A.T.C.C. deposit No. HB 10857.

5. A method for determining the presence of Hepatitis C Virus (HCV) antigen in a test sample which may contain HCV, comprising:
 a. contacting the test sample 7ith at least one anti-HCV E2/NS1 antibody attached to a solid phase which antibody specifically binds to HCV E2/NS1 antigen, to form a mixture;
 b. incubating said mixture for a time and under conditions sufficient to form antigen/antibody complexes;
 c. contacting said complexes with an indicator reagent comprising a signal generating compound 7hich generates a measurable detectable signal attached to an anti-HCV E2/NS1 antibody, to form a second mixture;
 d. incubating said second mixture for a time and under conditions sufficient to form antibody/antigen/antibody complexes; and
 e. determining the presence of HCV in the test sample by detecting the measurable signal generated, 7herein the amount of HCV present in the test sample is proportional to said measurable signal, wherein either the antibody specific for HCV E2/NS1 antigen of step (a) or of step (c) is a monoclonal antibody secreted by an A.T.C.C hybridoma cell line selected from the group consisting of A.T.C.C. deposit No. HB 10856 and A.T.C.C. deposit No. HB 10857.

6. The method of claim 5 wherein the signal generating compound is selected from the group consisting of a luminescent compound, a chemiluminescent compound, an enzyme and a radioactive element.

7. The method of claim 5 7herein the anti-HCV antibody attached to the solid phase is a polyclonal antibody.

8. The method of claim 5 wherein said anti-HCV E2/NS1 antibody attached to the solid phase is a monoclonal antibody.

9. The method of claim 5 7herein said indicator reagent comprises a signal generating compound attached to a polyclonal antibody.

10. The method of claim 5 7herein said indicator reagent comprises a signal generating compound attached to a monoclonal antibody.

11. A method for determining the presence and amount of Hepatitis C Virus (HCV) which may be present in a test sample, comprising:
 a. contacting a test sample 7ith a polyclonal anti-HCV E2/NS1 antibody attached to a solid phase and an indicator reagent comprising a monoclonal antibody 7hich specifically binds to HCV $E_2$/NS1 antigen attached to a signal generating compound 7hich generates a measurable detectable signal, to form a mixture, wherein said monoclonal antibody is a monoclonal antibody secreted by an A.T.C.C hybridoma cell line selected from the group consisting of A.T.C.C. deposit No. HB 10856 and A.T.C.C. deposit No. HB 10857;
 b. incubating said mixture for a time and under conditions sufficient to form antibody/antigen/antibody complexes; and
 c. determining the presence of HCV present in the test sample by detecting the measurable signal as an indication of the presence of HCV in the test sample, 7herein the amount of HCV present in the test sample is proportional to the measurable signal generated.

12. An assay kit for determining the presence of HCV antigen in a test sample, comprising:
 a container containing at least one monoclonal antibody which specifically binds to HCV E2/NS1 antigen, 7herein said monoclonal antibody is a monoclonal antibody secreted by an A.T.C.C hybridoma cell line selected from the group consisting of A.T.C.C. deposit No. HB 10856 and A.T.C.C. deposit No. HB 10857.

13. A method for determining the presence and amount of HCV which may be present in a test sample, comprising:
 a. contacting a test sample with a monoclonal anti-HCV E2/NS1 antibody attached to a solid phase and an indicator reagent comprising a polyclonal antibody 7hich specifically binds to HCV E2/NS1 attached to a signal generating compound which generates a measurable detectable signal, to form a mixture, 7herein said monoclonal antibody is a monoclonal antibody secreted by an A.T.C.C hybridoma cell line selected from the group consisting of A.T.C.C. deposit No. HB 10856 and A.T.C.C. deposit No. HB 10857;
 b. incubating said mixture for a time and under conditions sufficient to form antibody/antigen/antibody complexes; and
 c. determining the presence of HCV present in the test sample by detecting the measurable signal as an indication of the presence of HCV in the test sample, 7herein the amount of HCV present in the test sample is proportional to the measurable signal generated.

* * * * *